Figure 1:
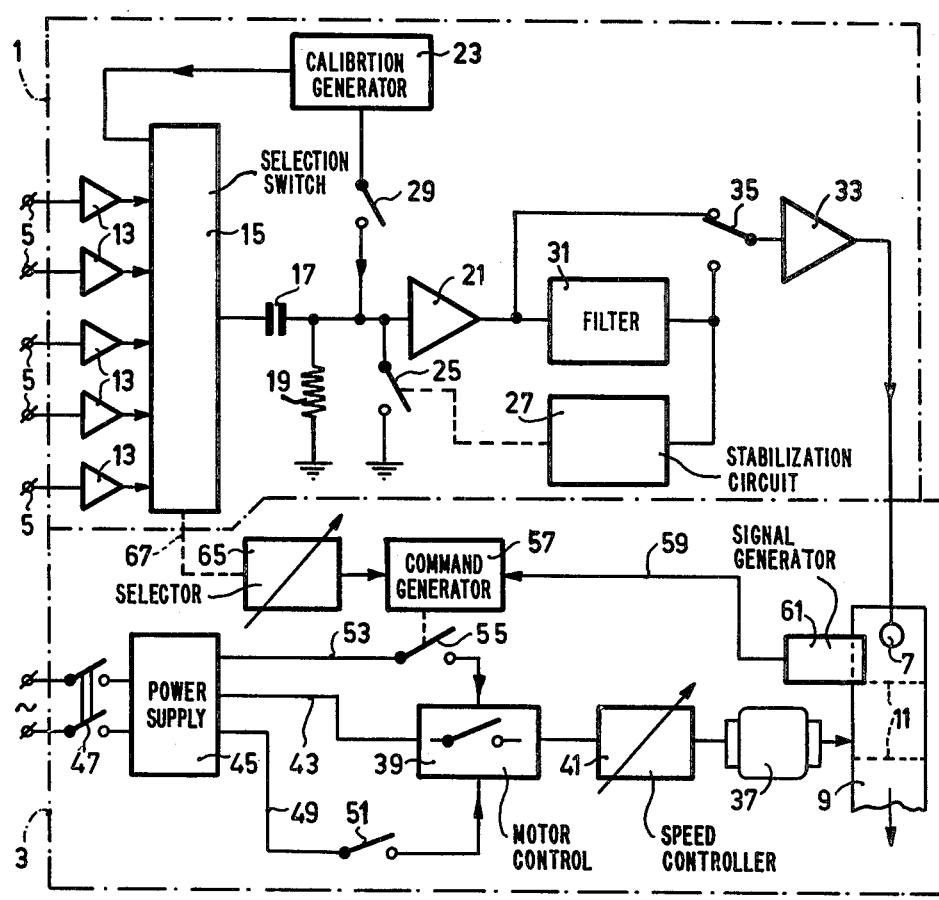

United States Patent [19]
Peyer

[11] 4,184,487
[45] Jan. 22, 1980

[54] ELECTROCARDIOGRAPH

[75] Inventor: Christoph Peyer, Belp, Switzerland

[73] Assignee: U.S. Philips Corporation, New York, N.Y.

[21] Appl. No.: 896,168

[22] Filed: Apr. 14, 1978

[30] Foreign Application Priority Data

Apr. 18, 1977 [NL] Netherlands .................... 7704185

[51] Int. Cl.² ............................................. A61B 5/04
[52] U.S. Cl. ............................. 128/710; 346/33 ME; 346/136
[58] Field of Search ...................... 128/2.06 G, 2.06 R, 128/2.05 Q, 2.05 R, 2.1 BR; 246/33 ME, 136

[56] References Cited

U.S. PATENT DOCUMENTS

| 3,568,812 | 3/1971 | Eitel | 346/136 |
| 3,579,248 | 5/1971 | McGrath, Jr. | 346/136 |
| 3,854,145 | 12/1974 | Carroll, Jr. et al. | 346/136 |
| 3,893,453 | 7/1975 | Goldberg et al. | 128/2.06 G |
| 3,946,744 | 3/1976 | Averbach | 128/2.06 A |

*Primary Examiner*—William E. Kamm
*Attorney, Agent, or Firm*—Thomas A. Briody; Edward J. Connors, Jr.; Jack E. Haken

[57] ABSTRACT

An electrocardiograph for recording electrocardiograms on fan-folded paper, comprising a manually operable derivation selection switch and a motor control member for the paper transport motor. The paper transport is automatically stopped when the recording stylus has passed an adjustable number of folds in the fan-folded paper.

3 Claims, 3 Drawing Figures

ELECTROCARDIOGRAPH

The invention relates to an electrocardiograph for recording an electrocardiogram on fan-folded paper, comprising a signal processing section, including a derivation selection switch and an ECG amplifier which controls a recording stylus, and also comprising a paper transport section, including a paper transport motor, a motor control member for switching the paper transport motor on and off, and a signal generator which is adapted to supply an indication signal each time when a fold in the fan-folded paper passes the stylus.

In a known electrocardiograph, the indication signal is applied to the derivation selection switch which switches over to a subsequent derivation each time when a fold in the paper passes the stylus. Thus, all preset derivations are successively recorded in accordance with a fixed program.

The known device has a drawback in that interventions in the program are not possible during recording, for example, changing of the preset derivations or repetition of a derivation. If an irregularity occurs during the completion of the program, for example, muscular movement of the patient or loosening of an electrode, the entire program must be repeated. The invention has for its object to provide an electrocardiograph which does not have these drawbacks.

To this end, the electrocardiograph in accordance with the invention is characterized in that the output of the signal generator is connected to a command generator which can be adjusted by means of a selection member and which is adapted to apply a "stop" command to the motor control member when the signal generator has supplied a predetermined number of indication signals after the switching on of the paper transport motor.

The invention will be described in detail hereinafter with reference to the accompanying diagrammatic drawing.

Figure 2:
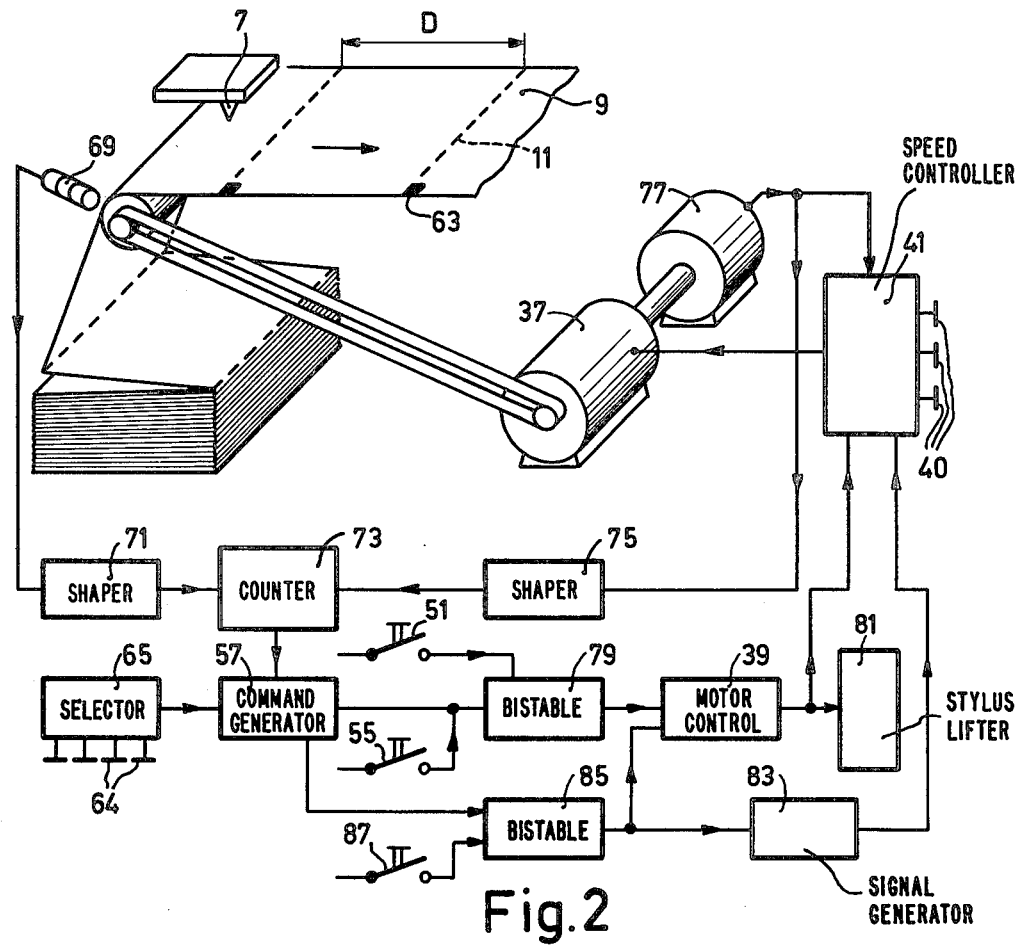
Figure 3:
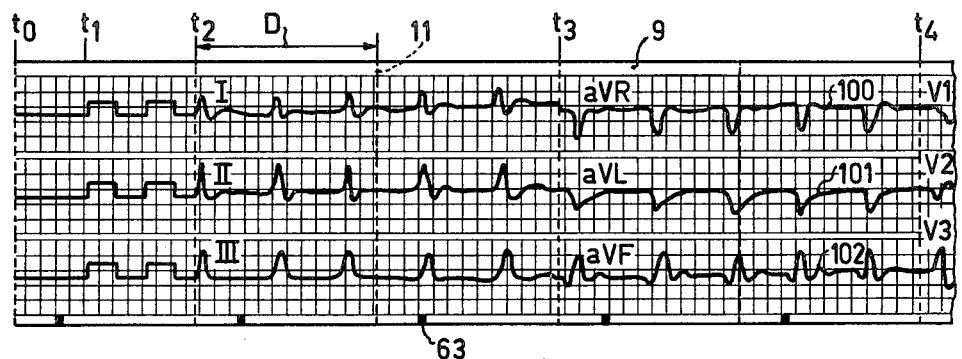

FIG. 1 shows a block diagram of an embodiment of an electrocardiograph in accordance with the invention, FIG. 2 shows a more detailed block diagram of a section of the electrocardiograph shown in FIG. 1, and FIG. 3 shows an example of an electrocardiogram recorded by means of the electrocardiograph in accordance with the invention.

The electrocardiograph which is diagrammatically shown in FIG. 1 comprises a signal processing section 1 and a paper transport section 3.

The signal processing section 1 is adapted to convert signals, originating from a number of electrodes 5 connected to a patient, into a control signal which determines the movement of a recording stylus 7 which records a visible recording trace on a fan-folded paper 9. Fan-folded paper is to be understood to mean recording paper which is provided at regular distances with a fold 11 which extends transversely of the longitudinal direction of the paper (denoted by a broken line), so that it is folded in a zigzag manner. The stylus 7 may be a known recording stylus which records a trace, by means of ink, heat or electrically, on a fan-folded paper 9 which is suitable for one of these recording methods.

The signals originating from the electrodes 5 are applied, via buffer amplifiers 13, to a derivation selection switch 15 by means of which different derivations commonly used in electrocardiography (for example, according to Einthoven, Wilson or Goldberger) can be selected. The output of the derivation selection switch 15 is applied, via a coupling network consisting of a capacitor 17 and a resistor 19, to a preamplifier 21. The derivation selection switch can be manually operated and besides a random choice of the various derivations, it offers the possibility of applying a calibration signal generated by a calibration generator 22 to the preamplifier 21. This calibration signal may consist, for example, of a direct voltage or squarewave voltage of 1 mV. The derivation selection switch furthermore comprises a position in which its output is at a fixed potential, so that no signal is applied to the preamplifier 21.

In order to enable undistorted reproduction of very low frequencies, the coupling network 17, 19 has a very long time constant. This means that after a large interference signal (for example, a switching surge due to the operation of the derivation selection switch 15 or interference due to the shifting of an electrode 5), the capacitor 17 maintains a high charge for a long period of time, so that the preamplifier 21 remains overdriven for a long period of time so that it cannot process signals. In order to prevent this phenomenon, there is provided a switch 25 whereby the resistor 19 can be temporarily short-circuited, so that the capacitor 17 is quickly discharged. The switch 25 can be operated by hand as well as via a known stabilization circuit 27. The stabilization circuit 27 automatically activates the switch 25 when the output signal of the preamplifier 21 exceeds a predetermined value.

A calibration signal originating from the calibration generator 23 can be added to the input signal of the preamplifier 21 by means of a manually operable switch 29.

The output signal of the preamplifier 21 is applied either directly or via a filter 31 to an ECG amplifier 33 which controls the stylus 7. The filter 31 limits the bandwidth of the ECG amplifier to 27 Hz in order to eliminate disturbing signals caused by vibrations of the mustles. It can be connected between the preamplifier 21 and the ECG amplifier 33 by means of a manually operated switch 35.

The paper transport section 3 comprises a paper transport motor 37 which can be switched on and off by means of a motor control 39. The paper transport speed can be adjusted by means of a speed controller 41 (for example, an adjustable voltage divider). The energy for the paper transportmotor 37 is supplied, via a lead 43, by a power supply 45 which is connected to the electrical mains by way of a mains switch 47. This power supply also supplies via a lead 49 and a manually operated switch 51, a "start" signal to the motor control unit and also supplies a "stop" signal to this unit, via a lead 53 and a switch, 55. In this embodiment, the switch 55 can be operated manually as well as by a command generator 57.

Via a lead 59, the command generator 57 receives an indication signal which is given by a signal generator 61 each time when a fold 11 in the fan-folded paper 9 passes the stylus 7.

The command generator 57 supplies the command "stop" by closing the switch 55 when the signal generator 61 has supplied a predetermined number of indication signals after the switching on of the motor 37. This number can be adjusted by means of a manually operated selection member 65.

Via a mechanical or electrical connection 67 (denoted by a broken line), the derivation selection switch 15 is coupled to the command generator 57 (directly or, as shown, via the selection member 65). This coupling ensures that when the derivation selection switch 15 is in a position in which no electrocardiogram is recorded, the command generator 57 supplies, regardless of the manually adjusted position of the selection member 65, the stop command when the next indication signal is received. Such positions of the derivation selection switch 15 are, for example, the positions in which the calibration signal originating from the calibration generator 23 or a fixed direct voltage is supplied to the capacitor 17.

FIG. 2 is a more detailed view of an embodiment of the paper transport section 3, the power supply unit 45 and the connections to the signal processing section 1 being omitted for the sake of simplicity; notably the signal generator 61 is elaborated. This generator of this embodiment comprises a photodetector 69 which supplies an electric pulse when it is passed by a black square 63 provided in the margin of the fan-folded paper. A square of this kind is provided at a fixed distance from each fold 11. The pulse supplied by the photodetector 69 is applied, via a pulse shaper 71 (for example, a monstable multivibrator), to a counter 73. This counter is adapted to count pulses which it receives, via a second pulse shaper 75, from a tachogenerator 77 which is coupled to the motor 37. The counter 73 is set to zero when it receives a pulse from the photodetector 69 and subsequently starts to count the pulses from the tachogenerator. When the counter 73 has counted a predetermined number of pulses, a fold 11 has arrived at the stylus 7 and the counter 73 supplies an indication signal to the command generator 57. This generator comprises a circuit for comparing the number of indication signals received with a number which is adjusted by means of pushbuttons 64 in the selection member 65. When the two numbers are equal, the command generator supplies a "stop" command, with the result that a bistable multivibrator 79, set to a first state by the "start" switch 51, switches over the second state. This bistable multivibrator is connected to the motor control member 39. The bistable multivibrator can also be set to the second state by means of the manually operated switch 55.

When the motor 37 is switched off, the motor control member 39, controlling the motor 37 via the speed controller 41, also supplies a signal to a stylus lifting device 81 which lifts the stylus 7 of the paper 9.

The speed controller 41 is manually operated by means of pushbuttons 40. Regardless of the position of these pushbuttons, however, it is adjusted for maximum paper transport speed when it receives a signal from a generator 83 which is switched on when a bistable multivibrator 85 reaches a first state by the closing of a switch 87. The switch 87 is depressed when recording is to be terminated. As has already been stated, the bistable multivibrator 85 then activates the generator 83, with the result that the paper 9 is transported at the maximum speed. The bistable multivibrator 85 is set to the second state when it receives a signal from the command generator 57. This generator supplies this signal when the counter 73 has counted a preset number of pulses from the tachogenerator 77. This number of pulses indicates that a fold 11 has been transported over a given distance beyond the stylus 7.

At the instant at which the bistable multivibrator 85 reaches the second state, it supplies a "stop" signal to the motor control member 39, with the result that the motor 37 stops. It also switches off the generator 83.

The paper 9 can then be readily torn at the fold 11 which is situated a given distance beyond the stylus 7. If desired, the paper 9 may be perforated at the area of the folds.

In the described embodiment, the signal generator 61 consists of the photodetector 69, the tachogenerator 77, the pulse shapers 71, 75 and the counter 73. Obviously, the passing of a fold 11 can also be signalled in an other manner. For example, the squares 63 may be replaced by punched holes which can be detected in a suitable manner.

In the embodiment described with reference to FIG. 1, there is only one amplifier circuit 21, 33 and only one stylus 7. It will be obvious that this number can be increased without objection, so that more than one derivation can be simultaneously recorded. FIG. 3 shows (at a reduced scale), a strip of fan-folded paper 9 on which three recording traces 100, 101, 102 are adjacently recorded. The distance D between two successive folds 11 actually amounts to 125 mm. The selection member 65 was adjusted so that the command generator 57 supplied a "stop" command each time after the reception of two indication signals from the signal generator 61. At the start of recording (instant $t_o$), the derivation selection switch 15 was in a position in which no signal was conducted (output earthed). At the instant $t_1$, a switch over took place to a position in which a squarewave voltage originating from the calibration generator 23 was conducted. This squarewave voltage was recorded on all three traces 100, 101, 102 until the instant $t_2$, when the command generator 57 supplied a "stop" command thanks to the connection 67. Subsequently, the derivation selection switch 15 was set to a position in which the derivations Einthoven I, II and III were recorded on the three recording traces 100, 101, 102, respectively, after which the paper transport motor 37 was switched on again by operation of the switch 52. At the instant $t_3$ (i.e., at the second fold 11), a "stop" command was given again by the command generator 57, after which the derivation selection switch 15 was set to a position in which the derivations Goldberger aVR, aVL and aVF were recorded on the three recording traces 100, 101, 102, respectively, followed by operation of the switch 51. At the instant $t_4$, a further "stop" command was given, followed by a switch over to a subsequent derivation. It will be obvious that the sequence in which the derivations are recorded can be chosen at random and that also the time during which a given derivation is recorded can be varied at random. The selection member 65, for example, may also include a position in which the command generator 57 does not supply a "stop" command. Recording then continues until the switch 55 is operated by hand. Conversely, a recording adjusted by means of the selection member 65 can also be prematurely interrupted by manual operation of the switch 55.

The switches, such as 51 and 55, may be, for example, mechanical switches, relays or semiconductor switches.

What is claimed is:

1. In an electrocardiograph for recording an electrocardiogram on fan-folded paper, which comprises a signal processing section, including a derivation selection switch and an ECG amplifier which controls a recording stylus, and a paper transport section, including a paper transport motor, motor control means which switch the paper transport motor on and off, and signal generator means which function to supply an indication signal each time when a fold in the fan-folded paper passes the stylus, the improvement wherein the output of the signal generator (61) is connected to a command generator (57) which is adjustable by means of selection means (65) and functions to apply a "stop" command to the motor control means (39) when the signal generator means (61) have supplied a predetermined number of indication signals following switching on of the paper transport motor (37).

2. An electrocardiograph as claimed in claim 1, wherein the derivation selection switch (15) is coupled to the command generator (57) so that, when the derivation selection switch (15) is in a position in which no electrocardiogram is recorded, the command generator (57) supplies a "stop" command when the next indication signal is received, regardless of a manually adjusted position of the selection means, (65).

3. An electrocardiograph as claimed in claim 1, wherein a mark (63) is provided at a fixed distance from each fold (11) in the fan-folded paper (9) and the signal generator (61) comprises a detector (69) which is adapted to supply a pulse each time one of said marks passes the detector, a tachogenerator (77) which is coupled to the paper transport motor (37) and which functions to supply a predetermined number of pulses per revolution of the motor (37), and counter means which function to count the number of pulses from the tachogenerator (77) which follow the last pulse received from the detector (69) and to supply an indication signal when the counted number of said pulses equals a predetermined number.

* * * * *